(12) United States Patent
Dai et al.

(10) Patent No.: US 12,358,914 B2
(45) Date of Patent: Jul. 15, 2025

(54) PREPARATION METHOD AND USE OF PYRAZOLE COMPOUND CONTAINING 1-(3,4-DIMETHOXYPHENYL)-β-CARBOLINE UNIT

(71) Applicant: NANTONG UNIVERSITY, Jiangsu (CN)

(72) Inventors: Hong Dai, Jiangsu (CN); Heyi Miao, Jiangsu (CN); Meiling Huang, Jiangsu (CN); Cheng Qian, Jiangsu (CN); Dandan Zheng, Jiangsu (CN); Yan Zhang, Jiangsu (CN); Yang Wang, Jiangsu (CN); Yong Ling, Jiangsu (CN); Beibei Zhou, Jiangsu (CN); Haijun Zhang, Jiangsu (CN)

(73) Assignee: NANTONG UNIVERSITY, Jiangsu (CN)

( * ) Notice: Subject to any disclaimer, the term of this patent is extended or adjusted under 35 U.S.C. 154(b) by 841 days.

(21) Appl. No.: 17/597,917

(22) PCT Filed: Aug. 25, 2021

(86) PCT No.: PCT/CN2021/114508
§ 371 (c)(1),
(2) Date: Jan. 28, 2022

(87) PCT Pub. No.: WO2022/042594
PCT Pub. Date: Mar. 3, 2022

(65) Prior Publication Data
US 2023/0357226 A1 Nov. 9, 2023

(30) Foreign Application Priority Data

Aug. 28, 2020 (CN) .......................... 202010882493.1

(51) Int. Cl.
*C07D 471/04* (2006.01)
*A61K 31/437* (2006.01)
*A61P 31/00* (2006.01)
*A61P 35/00* (2006.01)

(52) U.S. Cl.
CPC .......... *C07D 471/04* (2013.01); *A61K 31/437* (2013.01); *A61P 31/00* (2018.01); *A61P 35/00* (2018.01)

(58) Field of Classification Search
CPC ........ A61K 31/437; A61P 31/00; A61P 35/00; C07C 209/00; C07D 231/00; C07D 231/18; C07D 471/04
See application file for complete search history.

(56) References Cited

FOREIGN PATENT DOCUMENTS

| CN | 1418215 | A | | 5/2003 | |
|---|---|---|---|---|---|
| CN | 103228655 | A | | 7/2013 | |
| CN | 103596949 | A | | 2/2014 | |
| CN | 111892594 | A | * | 11/2020 | .............. A61P 35/00 |
| CN | 111892596 | A | * | 11/2020 | .............. A61P 35/00 |
| CN | 111961049 | A | * | 11/2020 | .............. A61P 35/00 |

OTHER PUBLICATIONS

"Synthesis and Herbicidal Activity Evaluation of Novel β-Carboline Derivatives," by Qunfang et al., Molecules 2012, 17(4), 3969-80. (Year: 2012).*
International Search Report issued to counterpart Application No. PCT/CN2021/114508 dated Nov. 23, 2021.
Li et al., "Discovery of novel β-carboline/acylhydrazone hybrids as potential antitumor agents and overcome drug resistance," European Journal of Medicinal Chemistry, vol. 152, May 7, 2018, p. 519, table 1, p. 517, scheme 1.
Guo et al., "Molecular hybrid design, synthesis, in vitro and in vivo anticancer evolution and mechanism of action of N-acylhydrazone linked, heterobivalent β-carbolines," Bioorganic Chemistry, vol. 96, Jan. 23, 2020, p. 103612.
Barbosa et al., "Synthesis and evaluation of novel hybrids β-carboline-4-thiazolidinones as potential antitumor and antiviral agents," European Journal of Medicinal Chemistry, vol. 124, Oct. 11, 2016, p. 1093-1104.
Chinese Office Action issued to counterpart Application No. 202010882493.1 dated Mar. 31, 2021.

\* cited by examiner

*Primary Examiner* — Theodore R. Howell
(74) *Attorney, Agent, or Firm* — McNees Wallace & Nurick LLC

(57) ABSTRACT

The disclosure relates to a preparation method and use of a pyrazole compound containing 1-(3,4-dimethoxyphenyl)-β-carboline unit. The pyrazole compound is prepared by reacting pyrazole aldehyde and 1-(3,4-dimethoxyphenyl)-β-carboline acylhydrazine. The pyrazole compound containing 1-(3,4-dimethoxyphenyl)-β-carboline unit has good inhibitory activity against tumor cell HGC-27. The pyrazole compound could be used in the preparation of anti-tumor drugs.

2 Claims, No Drawings

PREPARATION METHOD AND USE OF PYRAZOLE COMPOUND CONTAINING 1-(3,4-DIMETHOXYPHENYL)-β-CARBOLINE UNIT

CROSS REFERENCE TO RELATED APPLICATION(S)

This application claims the priority of Chinese Patent Application No. CN202010882493.1, entitled "Preparation method and use of pyrazole compound containing 1-(3,4-dimethoxyphenyl)-beta-carboline unit" filed with the Chinese National Intellectual Property Administration on Aug. 28, 2020, the disclosure of which is incorporated by reference herein in its entirety as part of the present application.

TECHNICAL FIELD

The present disclosure relates to the technical field of medicines, and in particular, to a preparation method and use of a pyrazole compound containing 1-(3,4-dimethoxyphenyl)-β-carboline unit.

BACKGROUND ART

Malignant tumors have threatened human health, and cancer has shown an upward trend year by year in terms of incidence rate. Therefore, there is a need for searching and discovering effective anti-cancer drugs and treatment methods.

β-carboline compounds, as an important member of the nitrogen-containing heterocyclic ring family, play an important role in medical care and have excellent inhibitory effect on some tumor cells.

Pyrazole derivatives are also an important type of nitrogen-containing heterocyclic unit, and also exhibit good inhibitory effect on many tumor cells.

It is of great significance to continue exploring drugs having good anti-tumor activity from pyrazole compounds.

SUMMARY

The first object of the present disclosure is to provide a pyrazole compound containing 1-(3,4-dimethoxyphenyl)-β-carboline unit, which exhibits inhibitory activity against HGC-27 tumor cells.

The second object of the present disclosure is to provide a method for preparing the pyrazole compound containing 1-(3,4-dimethoxyphenyl)-β-carboline unit as mentioned above.

The third object of the present disclosure is to provide use of the pyrazole compound containing 1-(3,4-dimethoxyphenyl)-β-carboline unit as mentioned above in the preparation of anti-tumor cell drugs.

In order to solve the above technical problems, the present disclosure provides a pyrazole compound containing 1-(3,4-dimethoxyphenyl)-β-carboline unit, which has the following structure:

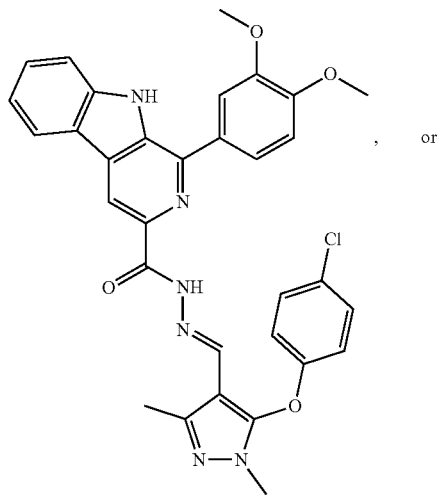

Ia, or

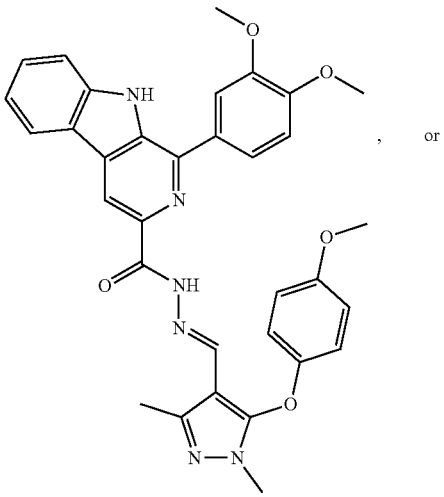

Ib, or

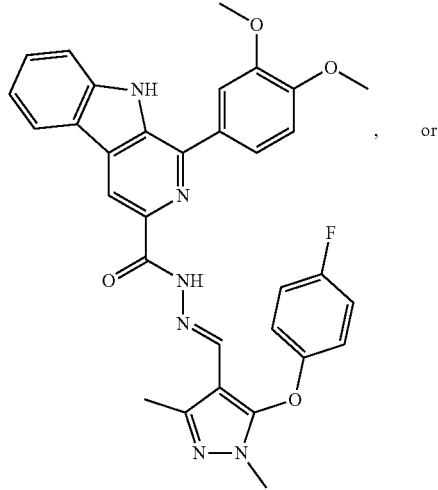

Ic, or

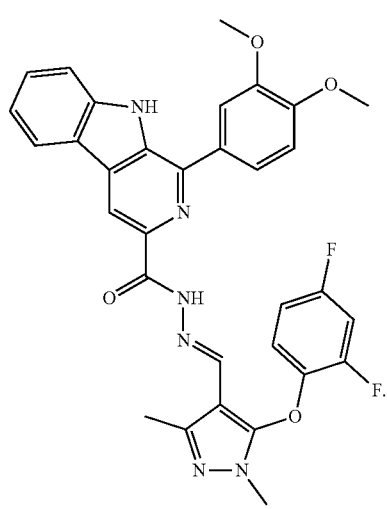
Id
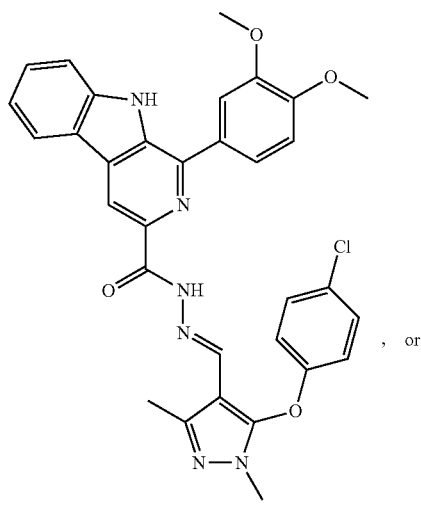
, or
Ia
The present disclosure provides a method for preparing the pyrazole compound containing 1-(3,4-dimethoxyphenyl)-β-carboline unit as mentioned above, including the following steps:
A method for preparing the pyrazole compound I containing 1-(3,4-dimethoxyphenyl)-β-carboline unit according to claim 1, characterized in that the method is as follows:
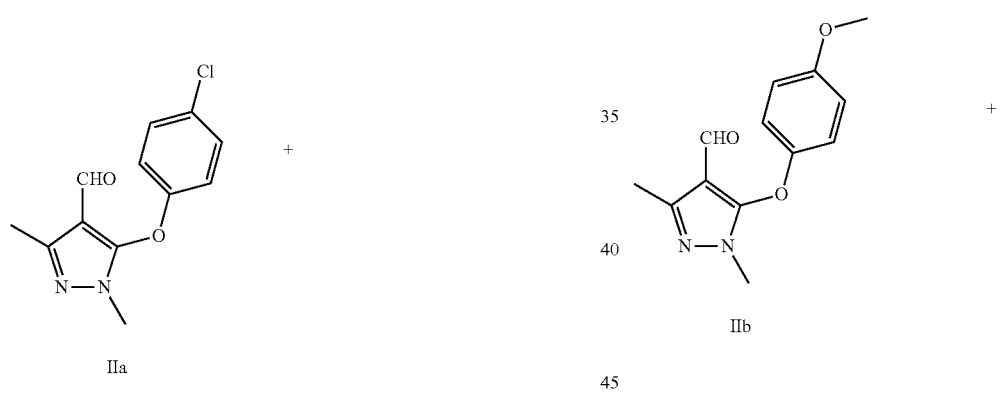
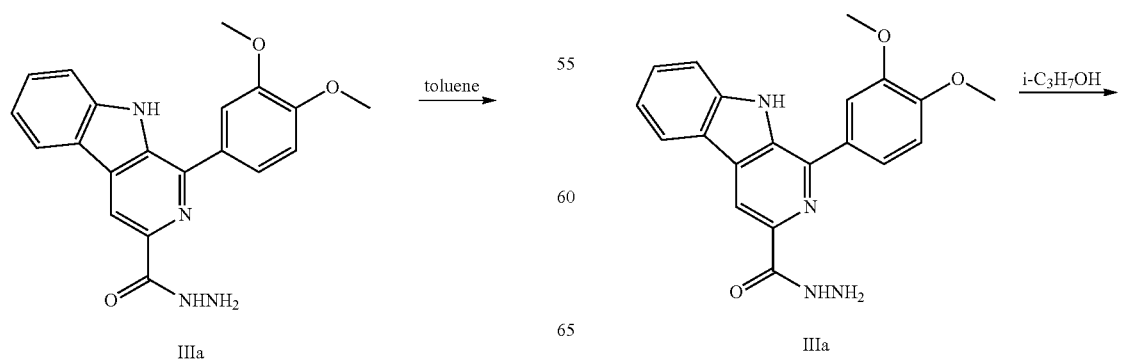

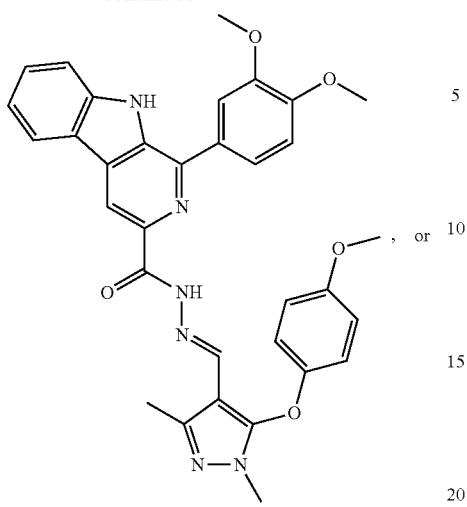
Ib
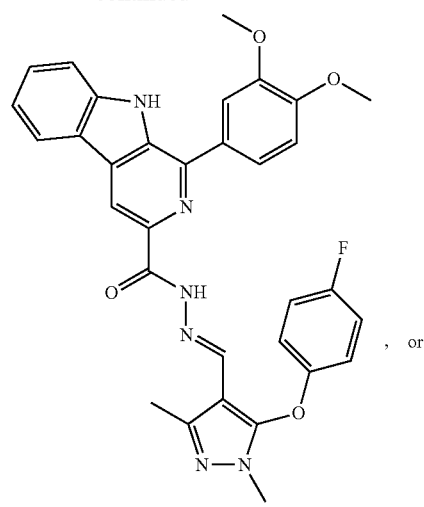
Ic
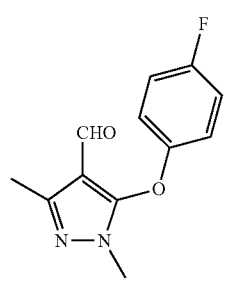
IIc
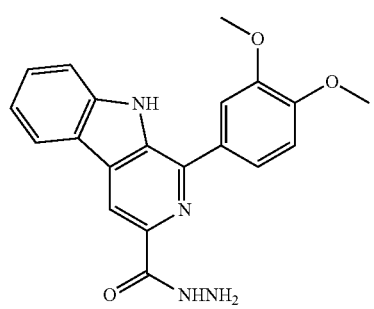
IId
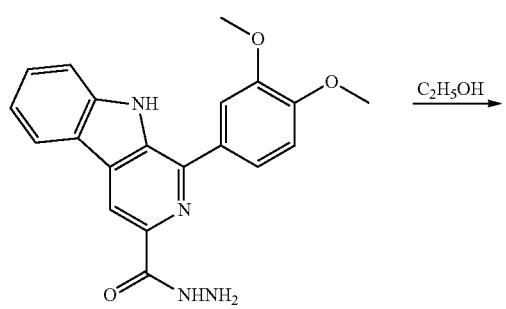
IIIa  →(DMF)
IIIa  →($C_2H_5OH$)

-continued

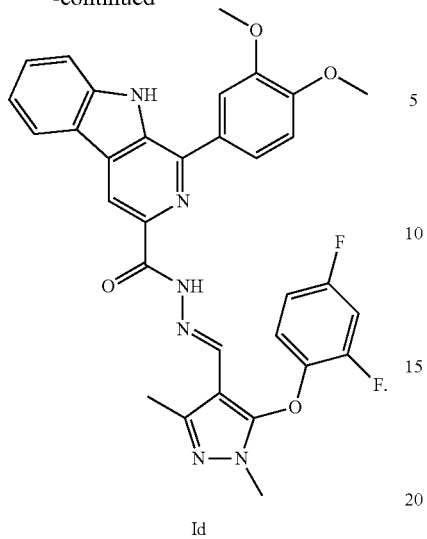

Id

Wherein, the intermediate pyrazole aldehyde is prepared according to the method described in the literature (Molecules 2017, 22, 2000), and the intermediate 1-(3,4-dimethoxyphenyl)-β-carboline acylhydrazine is prepared according to the method described in the literature (Chin. J. Org. Chem. 2016, 36, 1431).

In some embodiments, the method for preparing the pyrazole compound containing 1-(3,4-dimethoxyphenyl)-β-carboline unit having the structure of formula Ia comprises the following steps:

dissolving 15 mmol of an intermediate IIa in 30 mL of toluene, adding 19 mmol of an intermediate Ma thereto at room temperature to form a reaction solution, then heating the reaction solution to reflux and react for 13 hours, evaporating a solvent under reduced pressure, and purifying the resulting crude product by silica gel column chromatography to obtain the pyrazole compound containing 1-(3,4-dimethoxyphenyl)-β-carboline unit having the structure of formula Ia.

In some embodiments, the method for preparing the pyrazole compound containing 1-(3,4-dimethoxyphenyl)-β-carboline unit having the structure of formula Ib comprises the following steps:

dissolving 12 mmol of an intermediate IIb in 30 mL of isopropyl alcohol, adding 12 mmol of the intermediate Ma thereto at room temperature to form a reaction solution, then continuing stirring the reaction solution at room temperature for 20 hours, evaporating a solvent under reduced pressure, and purifying the resulting crude product by silica gel column chromatography to obtain the pyrazole compound containing 1-(3,4-dimethoxyphenyl)-β-carboline unit having the structure of formula Ib.

In some embodiments, the method for preparing the pyrazole compound containing 1-(3,4-dimethoxyphenyl)-β-carboline unit having the structure of formula Ic comprises the following steps:

dissolving 12 mmol of an intermediate IIc in 30 mL of DMF, adding 10 mmol of the intermediate Ma thereto at room temperature while stirring to form a reaction solution, then continuing stirring the reaction solution at room temperature for 28 hours, evaporating a solvent under reduced pressure, and purifying the resulting crude product by silica gel column chromatography to obtain the pyrazole compound containing 1-(3,4-dimethoxyphenyl)-β-carboline unit having the structure of formula Ic.

In some embodiments, the method for preparing the pyrazole compound containing 1-(3,4-dimethoxyphenyl)-β-carboline unit having the structure of formula Id comprises the following steps:

dissolving 10 mmol of an intermediate IId in 35 mL of ethanol, adding 11 mmol of the intermediate Ma thereto at room temperature to form a reaction solution, then heating the reaction solution to reflux and react for 10 hours, evaporating a solvent under reduced pressure, and purifying the resulting crude product by silica gel column chromatography to obtain the pyrazole compound containing 1-(3,4-dimethoxyphenyl)-β-carboline unit having the structure of formula Id.

The present disclosure provides use of the pyrazole compound I containing 1-(3,4-dimethoxyphenyl)-β-carboline unit described in the above technical solutions in the preparation of anti-tumor cell drugs, which is characterized in that the pyrazole compound I containing 1-(3,4-dimethoxyphenyl)-β-carboline unit exhibits inhibitory effect on HGC-27 tumor cells.

The pyrazole compound containing 1-(3,4-dimethoxyphenyl)-β-carboline unit according to the present disclosure exhibits good inhibitory activity against HGC-27 and other tumor cells.

The present disclosure makes substituted β-carboline and pyrazole active fragments be organically linked together, and discloses a class of pyrazole compounds containing 1-(3,4-dimethoxyphenyl)-β-carboline unit having medicinal value. The pyrazole compound containing 1-(3,4-dimethoxyphenyl)-β-carboline unit according to the present disclosure shows good inhibitory effect on tumor cell HGC-27, and thus could be used in the preparation of anti-tumor cell drugs.

DETAILED DESCRIPTION OF THE EMBODIMENTS

In order to facilitate a further understanding of the present disclosure, the following examples provide a more detailed description. These examples are for illustration only and are not intended to limit the scope or implementation principles of the present disclosure.

Example 1

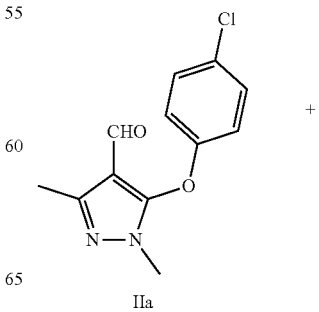

IIa

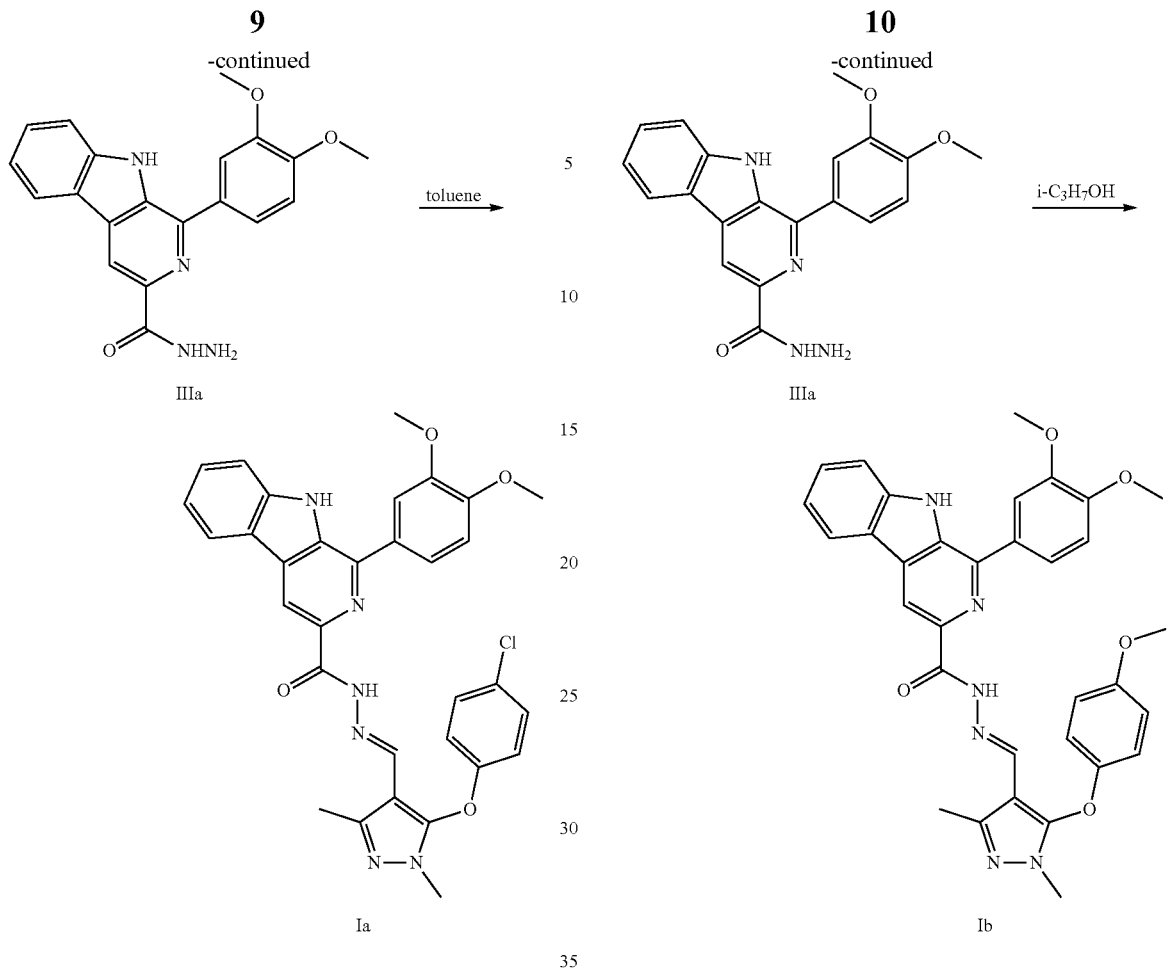

15 mmol of the intermediate IIa was dissolved in 30 mL of toluene, and 19 mmol of the intermediate Ma was added thereto at room temperature. The reaction solution was then heated to reflux and react for 13 hours. The solvent was evaporated under reduced pressure, and the resulting crude product was purified by silica gel column chromatography to obtain the target product Ia.

$^1$H NMR (400 MHz, CDCl$_3$): δ 11.85 (s, 1H, NH), 11.61 (s, 1H, NH), 8.82 (s, 1H, Ar—H), 8.43 (d, 1H, J=8.0 Hz, Ar—H), 8.36 (s, 1H, N=CH), 7.67-7.70 (m, 3H, Ar—H), 7.59 (t, 1H, J=7.2 Hz, Ar—H), 7.47 (d, 2H, J=8.8 Hz, Ar—H), 7.32 (t, 1H, J=7.2 Hz, Ar—H), 7.21 (d, 1H, J=8.0 Hz, Ar—H), 7.08 (d, 2H, J=8.8 Hz, Ar—H), 3.89 (d, 6H, J=7.2 Hz, CH$_3$), 3.57 (s, 3H, CH$_3$), 2.45 (s, 3H, CH$_3$).

12 mmol of the intermediate IIb was dissolved in 30 mL of isopropyl alcohol, and 12 mmol of the intermediate Ma was added thereto at room temperature. The reaction solution was then continued stirring at room temperature for 20 hours. The solvent was evaporated under reduced pressure, and the resulting crude product was purified by silica gel column chromatography to obtain the target product Ib.

$^1$H NMR (400 MHz, CDCl$_3$): δ 11.85 (s, 1H, NH), 11.60 (s, 1H, NH), 8.82 (s, 1H, Ar—H), 8.43 (d, 1H, J=8.0 Hz, Ar—H), 8.35 (s, 1H, N=CH), 7.68-7.70 (m, 3H, Ar—H), 6.70 (t, 1H, J=7.2 Hz, Ar—H), 7.32 (t, 1H, J=7.2 Hz, Ar—H), 7.21 (d, 1H, J=8.4 Hz, Ar—H), 6.93-7.00 (m, 4H, Ar—H), 3.90 (d, 6H, J=5.2 Hz, CH$_3$), 3.71 (s, 3H, CH$_3$), 3.56 (s, 3H, CH$_3$), 2.45 (s, 3H, CH$_3$).

Example 2

Example 3

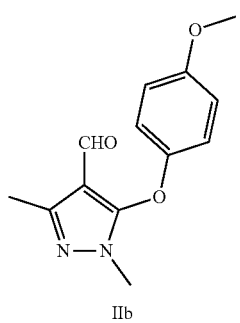

IIb

+

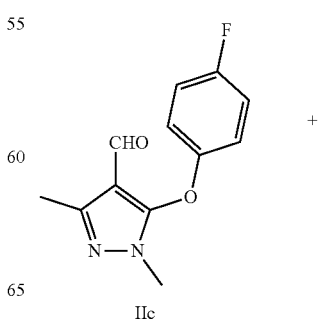

IIc

+

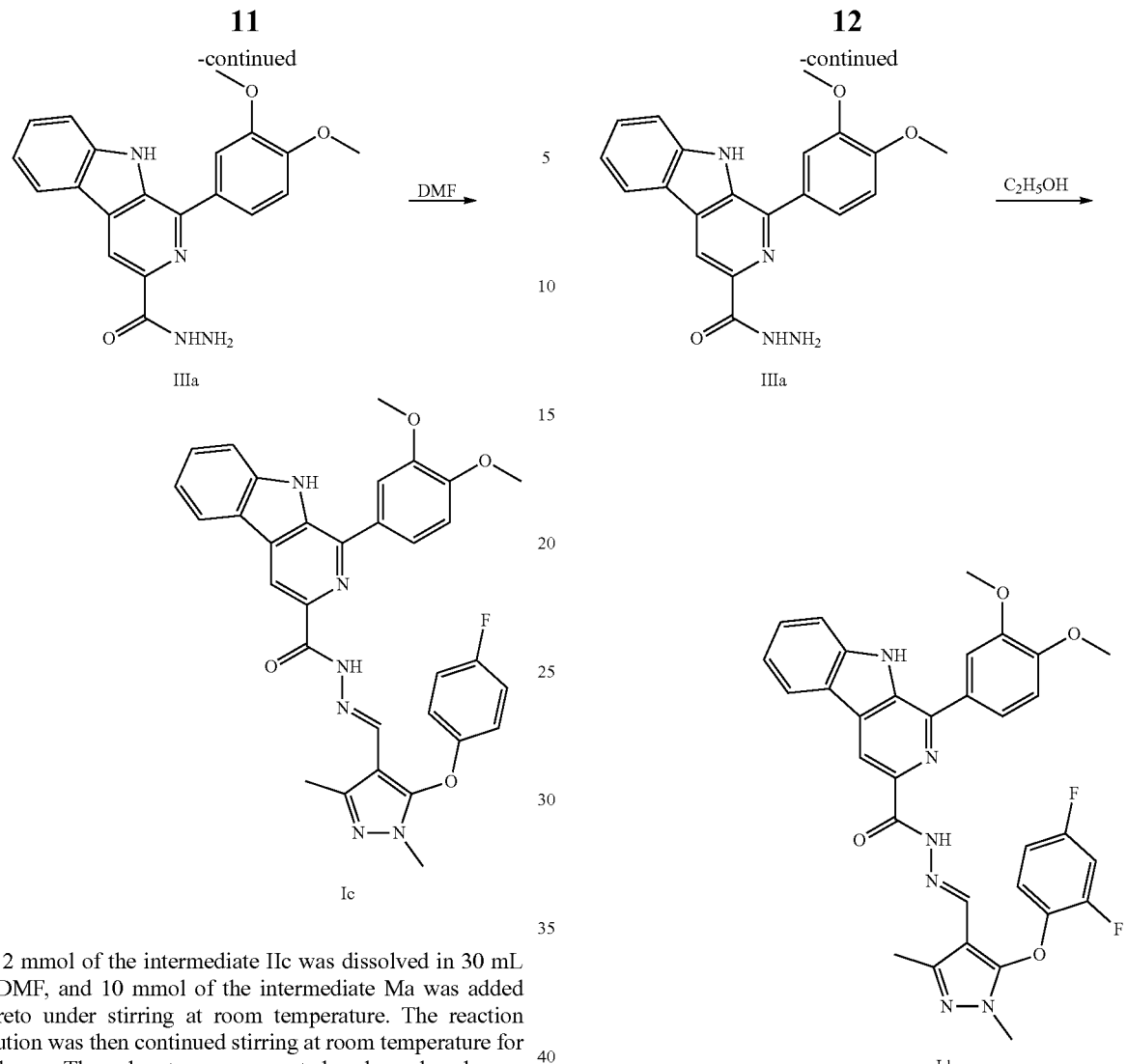

12 mmol of the intermediate IIc was dissolved in 30 mL of DMF, and 10 mmol of the intermediate IIIa was added thereto under stirring at room temperature. The reaction solution was then continued stirring at room temperature for 28 hours. The solvent was evaporated under reduced pressure, and the resulting crude product was purified by silica gel column chromatography to obtain the target product Ic.

$^1$H NMR (400 MHz, CDCl$_3$): δ 11.86 (s, 1H, NH), 11.61 (s, 1H, NH), 8.82 (s, 1H, Ar—H), 8.43 (d, 1H, J=8.0 Hz, Ar—H), 8.36 (s, 1H, N=CH), 7.67-7.70 (m, 3H, Ar—H), 7.59 (t, 1H, J=7.6 Hz, Ar—H), 7.32 (t, 1H, J=7.6 Hz, Ar—H), 7.19-7.27 (m, 3H, Ar—H), 7.07-7.11 (m, 2H, Ar—H), 3.90 (d, 6H, J=4.8 Hz, CH$_3$), 3.58 (s, 3H, CH$_3$), 2.45 (s, 3H, CH$_3$).

Example 4

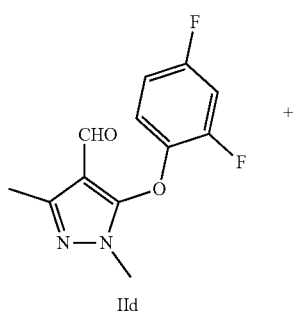

IId 10 mmol of the intermediate IId was dissolved in 35 mL of ethanol, and 11 mmol of the intermediate IIIa was added thereto at room temperature. The reaction solution was then heated to reflux and react for 10 hours. The solvent was evaporated under reduced pressure, and the resulting crude product was purified by silica gel column chromatography to obtain the target product Id.

$^1$H NMR (400 MHz, CDCl$_3$): δ 11.86 (s, 1H, NH), 11.59 (s, 1H, NH), 8.83 (s, 1H, Ar—H), 8.43 (d, 1H, J=7.6 Hz, Ar—H), 8.35 (s, 1H, N=CH), 7.67-7.71 (m, 3H, Ar—H), 7.51-7.62 (m, 2H, Ar—H), 7.32 (t, 1H, J=7.2 Hz, Ar—H), 7.22 (d, 1H, J=8.4 Hz, Ar—H), 7.02-7.05 (m, 2H, Ar—H), 3.92 (d, 6H, J=10.0 Hz, CH$_3$), 3.63 (s, 3H, CH$_3$), 2.42 (s, 3H, CH$_3$).

Example 5

Anti-Tumor Activity Test of Compounds

The in-vitro anti-tumor activity of the compounds was tested by tetramethylazoazole colorimetric (MTT) method. Human gastric cancer cell HGC-27 was used as a test cell. 5-fluorouracil (5-FU) was selected as the positive control drug. Human gastric cancer cell HGC-27 in the exponential growth phase was made into a cell suspension with 4×10$^3$ cells/mL, inoculated in a 96-well plate, and cultured in a $CO_2$ incubator for 36 hours. The test solution (10 μL) of the compound to be tested was added into the test wells, with parallel wells being set for each concentration. The same amount of DMSO was used as a blank control. The plate was incubated in a $CO_2$ incubator for 24 hours, then the supernatant was discarded, and 10 μL of 5% MTT was added to each well. Then the plate was incubated for 4 hours, and the supernatant was sucked and discarded. Subsequently, 100 μL of DMSO was added to each well, and the plate was shaken in a shaker for 20 minutes. The OD value was measured with a microplate reader at a wavelength of 570 nm, and the cell inhibition rate was calculated. Cell inhibition rate=(OD value of negative control group−OD value of tested substance group)/OD value of negative control group×100%. The $IC_{50}$ value of each compound was calculated by the probability unit weighted regression method.

TABLE 1

Data of anti-tumor activity of compounds Ia-Id ($IC_{50}$, μM)

| Compounds | HGC-27 |
| --- | --- |
| Ia | 10.10 |
| Ib | 1.89 |
| Ic | 7.03 |
| Id | 1.27 |
| 5-FU | 34.10 |

As can be seen from the data in Table 1, all the compounds Ia-Id show good anti-tumor activity against human gastric cancer cell HGC-27, which is better than the anti-tumor effect of the positive control drug 5-fluorouracil (5-FU). The above experimental results show that by organically linking substituted β-carboline and pyrazole active fragment, the prepared compound has a good anti-tumor effect on the human gastric cancer cell HGC-27.

The above examples are merely intended to assist in understanding the method and core concepts of the present disclosure. It should be noted that those of ordinary skill in the art may make a number of improvements or refinements without departing from the principle of the present disclosure. These improvements or refinements should also fall within the scope of the claims of the present disclosure. Various modifications to these examples will be apparent to those skilled in the art, and the general principles defined herein could be implemented in other embodiments without departing from the spirit or scope of the present disclosure. Therefore, the present disclosure are not limited to these examples shown herein, but will conform to the widest scope consistent with the principles and novel features disclosed herein.

What is claimed is:

1. A pyrazole compound I containing 1-(3,4-dimethoxyphenyl)-β-carboline unit, wherein the pyrazole compound has a structure shown in formulas Ia-Id:

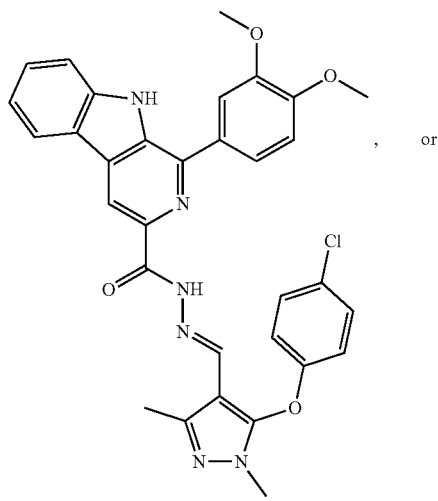

Ia , or

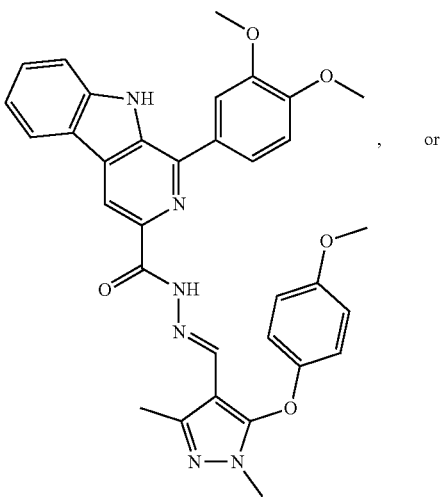

Ib , or

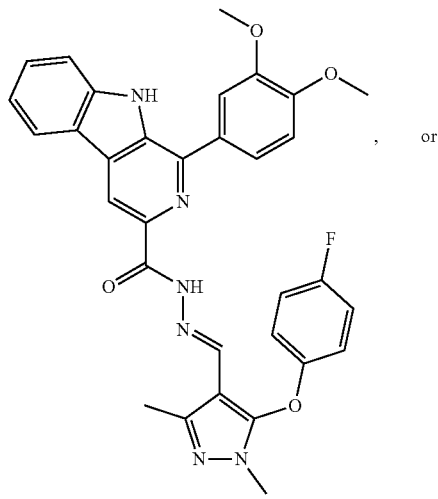

Ic , or

15
-continued
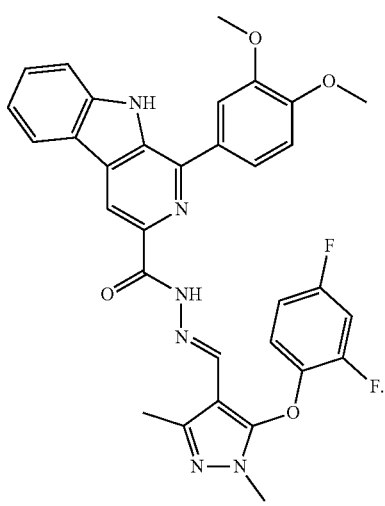
Id
16
-continued
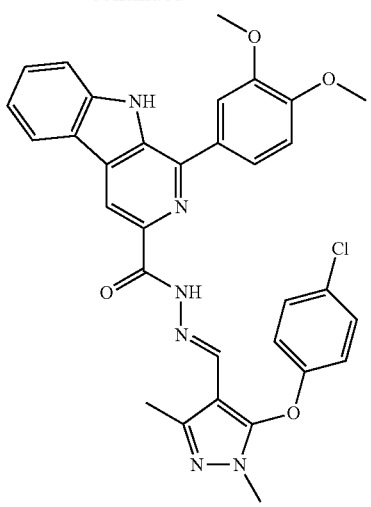
Ia
, or
2. A method for preparing the pyrazole compound I containing 1-(3,4-dimethoxyphenyl)-β-carboline unit as claimed in claim 1, the method being as follows:
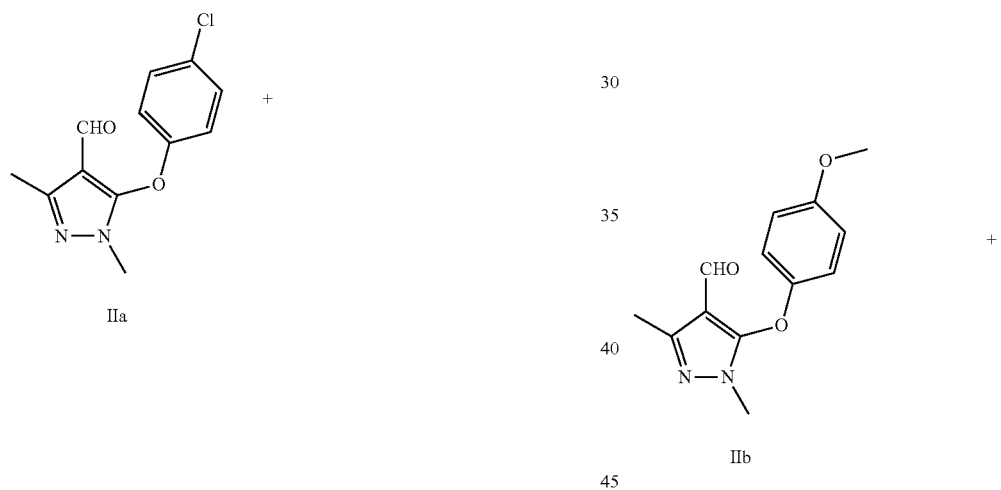
IIa
IIb
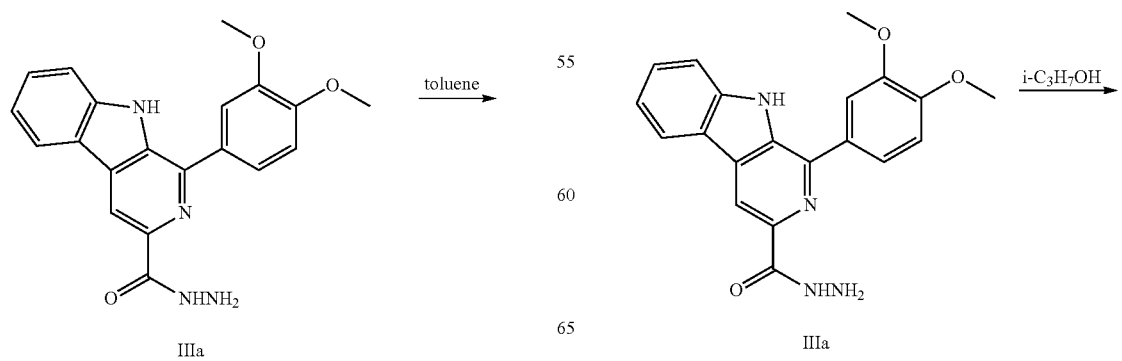
IIIa
toluene
IIIa
i-C₃H₇OH

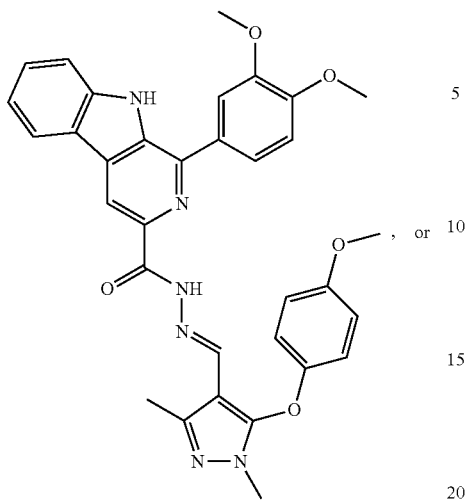
Ib
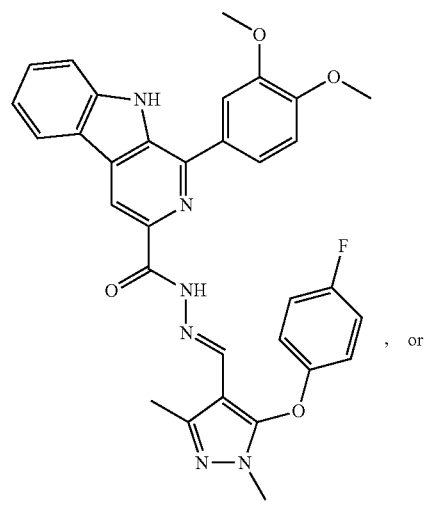
Ic
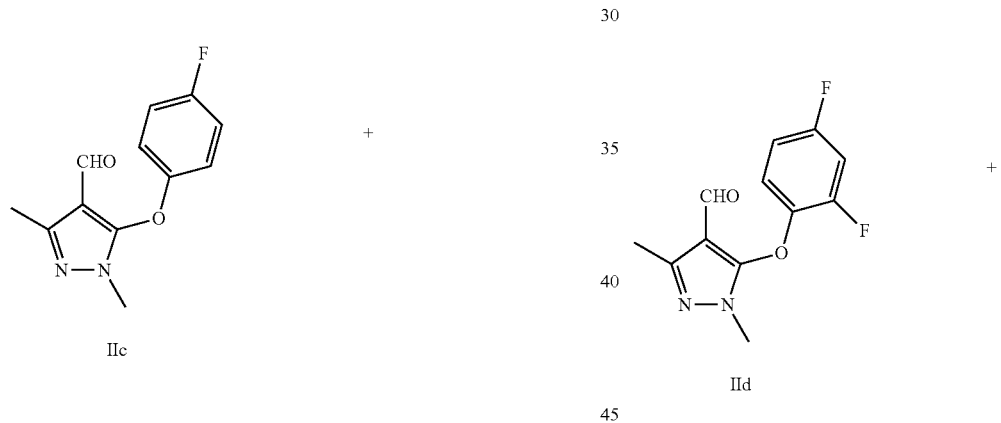
IIc                     IId
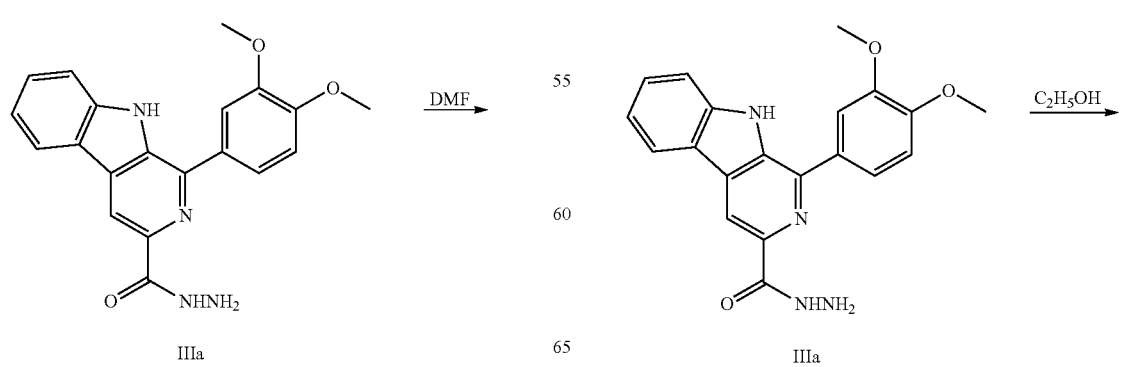
IIIa                    IIIa -continued

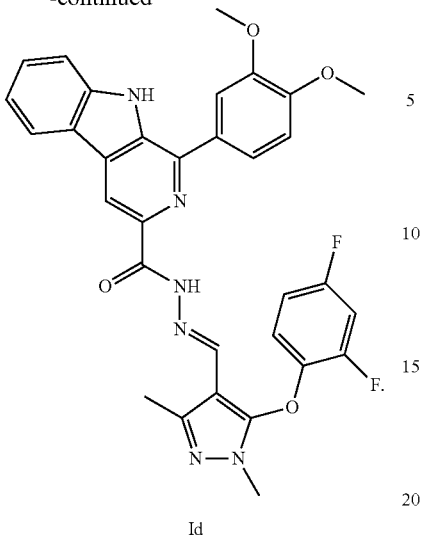

Id wherein the method for preparing the pyrazole compound containing 1-(3,4-dimethoxyphenyl)-β-carboline unit having the structure of formula Ia comprises the following steps:
dissolving 15 mmol of an intermediate IIa in 30 mL of toluene,
adding 19 mmol of an intermediate IIIa thereto at room temperature to form a reaction solution,
heating the reaction solution to reflux and react for 13 hours,
evaporating a solvent under reduced pressure, and
purifying the resulting crude product by silica gel column chromatography to obtain the pyrazole compound containing 1-(3,4-dimethoxyphenyl)-β-carboline unit having the structure of formula Ia;
wherein the method for preparing the pyrazole compound containing 1-(3,4-dimethoxyphenyl)-β-carboline unit having the structure of formula Ib comprises the following steps:
dissolving 12 mmol of an intermediate IIb in 30 mL of isopropyl alcohol,
adding 12 mmol of the intermediate IIIa thereto at room temperature to form a reaction solution,
continuing stirring the reaction solution at room temperature for 20 hours,
evaporating a solvent under reduced pressure, and
purifying the resulting crude product by silica gel column chromatography to obtain the pyrazole compound containing 1-(3,4-dimethoxyphenyl)-β-carboline unit having the structure of formula Ib;
wherein the method for preparing the pyrazole compound containing 1-(3,4-dimethoxyphenyl)-β-carboline unit having the structure of formula Ic comprises the following steps:
dissolving 12 mmol of an intermediate IIc in 30 mL of DMF,
adding 10 mmol of the intermediate IIIa thereto while stirring at room temperature to form a reaction solution,
continuing stirring the reaction solution at room temperature for 28 hours,
evaporating a solvent under reduced pressure, and
purifying the resulting crude product by silica gel column chromatography to obtain the pyrazole compound containing 1-(3,4-dimethoxyphenyl)-β-carboline unit having the structure of formula Ic; and
wherein the method for preparing the pyrazole compound containing 1-(3,4-dimethoxyphenyl)-β-carboline unit having the structure of formula Id comprises the following steps:
dissolving 10 mmol of an intermediate IId in 35 mL of ethanol,
adding 11 mmol of the intermediate IIIa thereto at room temperature to form a reaction solution,
heating the reaction solution to reflux and react for 10 hours,
evaporating a solvent under reduced pressure, and
purifying the resulting crude product by silica gel column chromatography to obtain the pyrazole compound containing 1-(3,4-dimethoxyphenyl)-β-carboline unit having the structure of formula Id.

* * * * *